(12) United States Patent
Rajan et al.

(10) Patent No.: US 11,998,710 B2
(45) Date of Patent: Jun. 4, 2024

(54) APPLICATOR FOR DELIVERY OF A PRODUCT THERETHROUGH

(71) Applicant: Church & Dwight Co., Inc., Princeton, NJ (US)

(72) Inventors: Sujata Sundara Rajan, Belle Mead, NJ (US); Ming Zeng, Princeton, NJ (US); Jonathan Andrew Wharton, Ewing, NJ (US); Timothy Snowden, Howell, NJ (US); Pamela Dozier, Doylestown, PA (US); Brian Orme, Phoenixville, PA (US); Meredith Ingrassia, North Wales, PA (US)

(73) Assignee: Church & Dwight Co., Inc., Princeton, NJ (US)

( * ) Notice: Subject to any disclaimer, the term of this patent is extended or adjusted under 35 U.S.C. 154(b) by 361 days.

(21) Appl. No.: 17/218,464

(22) Filed: Mar. 31, 2021

(65) Prior Publication Data

US 2021/0308437 A1    Oct. 7, 2021

Related U.S. Application Data

(60) Provisional application No. 63/003,586, filed on Apr. 1, 2020.

(51) Int. Cl.
*A61M 31/00*    (2006.01)

(52) U.S. Cl.
CPC ......... *A61M 31/00* (2013.01); *A61M 2202/04* (2013.01); *A61M 2210/1475* (2013.01)

(58) Field of Classification Search
CPC .............. A61M 31/00; A61M 2202/04; A61M 2210/1475
See application file for complete search history.

(56) References Cited

U.S. PATENT DOCUMENTS

| 2,690,181 A | 9/1954 | Boyer |
| 3,074,115 A | 1/1963 | Albrecht et al. |

(Continued)

FOREIGN PATENT DOCUMENTS

| CN | 303317444 | 8/2015 |
| CN | 106139378 | 11/2016 |

(Continued)

OTHER PUBLICATIONS

Extended European Search Report issued Apr. 10, 2024, in corresponding European application No. 217808887.2.

*Primary Examiner* — Quynh-Nhu H. Vu
(74) *Attorney, Agent, or Firm* — Church & Dwight Co., Inc.

(57) ABSTRACT

The present disclosure provides applicators adapted to or configured to deliver a product therefrom. The applicators can be particularly designed for delivery to certain body parts of the human body, such as to the vaginal area. The applicator can comprise a housing formed of a substantially continuous wall extending along a longitudinal housing axis between a base end and an application end, the substantially continuous wall defining: a base segment extending from the base end toward the applicator end; a delivery segment extending from the applicator end toward the base end; and a compression segment interconnecting the base segment and the delivery segment. The housing can define a substantially hollow interior configured for retaining a product for delivery through the delivery segment.

21 Claims, 4 Drawing Sheets

(56) References Cited

U.S. PATENT DOCUMENTS

| | | | |
|---|---|---|---|
| 3,570,662 A | 3/1971 | Polyak | |
| 3,777,949 A * | 12/1973 | Chiquiari-Arias | B65D 35/36 |
| | | | 401/132 |
| D236,235 S | 8/1975 | Payton | |
| 4,358,028 A | 11/1982 | Chiquiar-Arias | |
| D300,561 S | 4/1989 | Asa et al. | |
| 5,006,004 A * | 4/1991 | Dirksing | A45D 34/042 |
| | | | 401/265 |
| D345,211 S | 3/1994 | Bologna | |
| 5,320,257 A * | 6/1994 | Snedden | B65D 1/095 |
| | | | 222/215 |
| D375,352 S | 11/1996 | Bologna | |
| D403,960 S | 1/1999 | Stromblad et al. | |
| 6,443,330 B1 | 9/2002 | Kuboshima | |
| 6,537,260 B1 * | 3/2003 | Lamb | A61M 3/0262 |
| | | | 604/279 |
| 6,626,308 B2 | 9/2003 | Weiler | |
| D518,891 S | 4/2006 | Strong | |
| D601,908 S | 10/2009 | Yun | |
| 8,870,836 B2 | 10/2014 | Sweeney | |
| D803,054 S | 11/2017 | Van Spronsen | |
| D859,647 S | 9/2019 | Chang | |
| D882,272 S | 4/2020 | Celia, Jr. | |
| D884,481 S | 5/2020 | Lim et al. | |
| 2008/0051740 A1 * | 2/2008 | Sokal | A61P 15/18 |
| | | | 514/789 |
| 2009/0131874 A1 | 5/2009 | Maki et al. | |
| 2011/0087172 A1 | 4/2011 | Gunderson | |
| 2017/0197069 A1 | 7/2017 | Habig et al. | |
| 2017/0304599 A1 | 10/2017 | Dombrowski et al. | |
| 2018/0221634 A1 * | 8/2018 | Hazan | A61F 2/0022 |

FOREIGN PATENT DOCUMENTS

| | | |
|---|---|---|
| EP | 1588734 | 10/2005 |
| GB | 2018233 | 10/1979 |
| JP | D1306289 | 6/2007 |
| WO | WO 2006/132579 | 12/2006 |

* cited by examiner

APPLICATOR FOR DELIVERY OF A PRODUCT THERETHROUGH

CROSS-REFERENCE TO RELATED APPLICATIONS

The present application claims priority to U.S. Provisional Patent Application No. 63/003,586, filed Apr. 1, 2020, the disclosure of which is incorporated herein by reference.

FIELD OF THE DISCLOSURE

The present disclosure relates to applicators that are adapted to or configured to deliver a product therethrough. More particularly, the applicators can be adapted to or configured to deliver liquids at a variety of viscosities for easy delivery to various parts of the body.

BACKGROUND

Applicator devices are commonly used for delivery of a product to a site of use without the requirement of the user physically touching the product being delivered. For example, in the field of consumer products designed for use in or on the human body, it can be desirable to provide the products in a container with an application attached or attachable thereto so that the consumer may easily apply the product to a part of the body with necessarily touching the product with their hands. It has been difficult in the past, however, to provide liquid products in particular that may be easily applied over a range of product viscosities. For example, relatively low viscosity liquids may have a tendency to be over-applied or to be inadvertently leaked during application. Likewise, relatively high viscosity liquids may require excessive force to pass through an applicator. It further can be difficult to provide an applicator that is desirably small and discrete while also being easy to grasp and manipulate for delivery of the product. Accordingly, there remains a need in the field for applicator devices providing for improved ease of use.

SUMMARY OF THE DISCLOSURE

The present disclosure provides applicators that are adapted to or configured to deliver a product therethrough. More particularly, the applicators can be adapted to or configured to deliver liquids at a variety of viscosities for easy delivery to various parts of the body. The present applicators are specifically useful for improving the ease of delivery of the product to a body part, such as the vaginal area, where it may not be particularly easy to both properly locate the applicator while simultaneously manipulating the applicator to achieve delivery of the product therefrom. Such delivery can be complicated further when the product for delivery is a relatively viscous liquid that can require significant, manual force to expel the liquid from the applicator. The presently disclosed applicators can include a combination of elements that simplify such product delivery.

In one or more embodiments, the present disclosure thus can relate to applicators adapted to or configured to deliver a product therefrom. For example, such applicators can comprise: a housing formed of a substantially continuous wall extending along a longitudinal housing axis between a base end having a first cross-wise dimension and an application end having a second cross-wise dimension that is less than the first cross-wise dimension, the substantially continuous wall defining: a base segment extending from the base end toward the applicator end; a delivery segment extending from the applicator end toward the base end; and a compression segment interconnecting the base segment and the delivery segment; wherein the housing defines a substantially hollow interior configured for retaining a product for delivery through the delivery segment. In further embodiments, such applicator(s) can be defined in relation to one or more of the following statements, which can be combined in any number and order.

The substantially continuous wall can comprise an exterior surface, and wherein at least a portion of the exterior surface of the base segment includes raised texturing thereon.

The raised texturing can be aligned substantially orthogonally to the longitudinal housing axis.

The substantially continuous wall can have a thickness that varies along a length of the longitudinal housing axis.

The substantially continuous wall can have a thickness in the compression segment that is less than a thickness of the substantially continuous wall in one or both of the base segment and the delivery segment.

The substantially continuous wall in the compression segment can be substantially curvilinear along the longitudinal housing axis.

The substantially continuous wall in one or both of the base segment and the delivery segment can be substantially linear along the longitudinal housing axis.

The housing has a total length, and wherein the delivery segment can form about 50% or greater of the total length of the housing.

The base segment can comprise about 40% or less of the total length of the housing.

The compression segment can comprise about 5% to about 30% of the total length of the housing.

The base segment can be configured to have an internal volume of about 5 $cm^3$ to about 100 $cm^3$.

The applicator can be configured for delivery of a liquid product having a viscosity of about 100 cP to about 300,000 cP.

The applicator further comprises a removable closure positioned at the application end of the housing.

The removable closure can be configured as a twist-off tab.

The twist-off tab can have a height that is substantially parallel to the longitudinal housing axis and a width that is substantially transverse to the longitudinal housing axis.

The width of the twist-off tab can be greater than the second cross-wise dimension of the housing at the application end of the housing.

The width of the twist-off tab can be about 5% to about 100% of the first cross-wise dimension of the housing at the base end of the housing.

The housing can have a substantially round cross-section.

The base end of the applicator can have a substantially linear seal.

The housing can be pre-filled with a liquid product.

The liquid product can be a vaginal lubricant.

DETAILED DESCRIPTION OF THE DISCLOSURE

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

Figure 1:
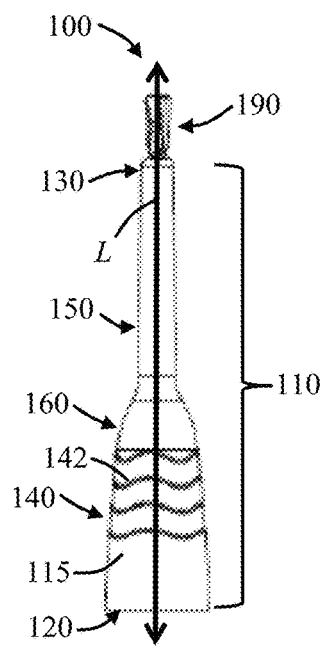
FIG. 1 is an elevational view of an applicator according to an example embodiment of the present disclosure.
Figure 2:
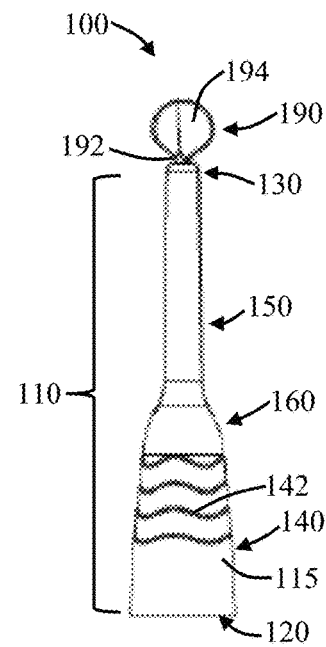
FIG. 2 is an elevational view of the applicator of FIG. 1 rotated 90 degrees relative to the view of FIG. 1.
Figure 3:
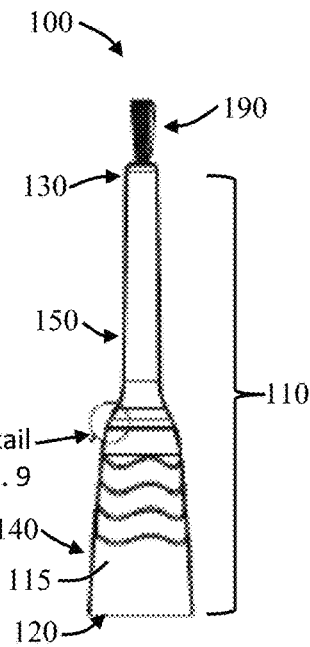
FIG. 3 is a cross-sectional view of the applicator of FIG. 1.
Figure 4:
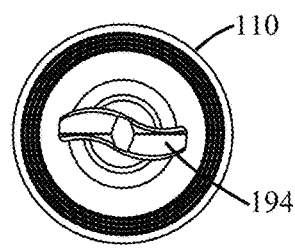
FIG. 4 is a top view of the applicator of FIG. 1.
Figure 5:
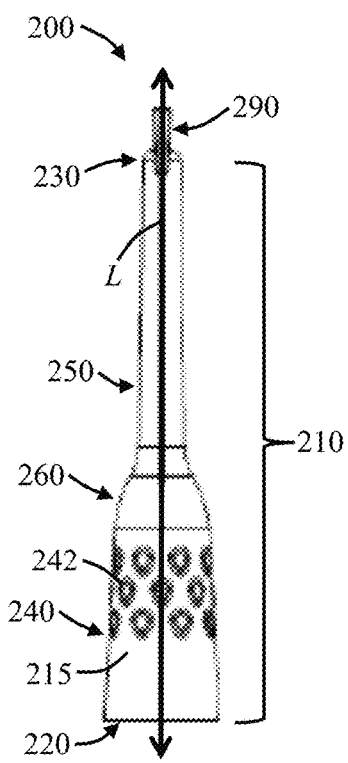
FIG. 5 is an elevational view of an applicator according to another example embodiment of the present disclosure.
Figure 6:
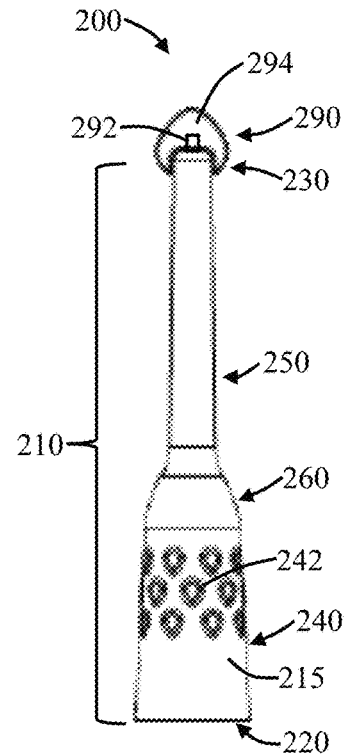
FIG. 6 is an elevational view of the applicator of FIG. 5 rotated 90 degrees relative to the view of FIG. 5.
Figure 7:
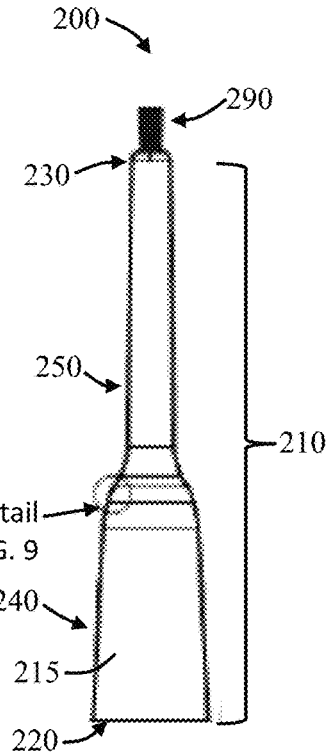
FIG. 7 is a cross-sectional view of the applicator of FIG. 5.
Figure 8:
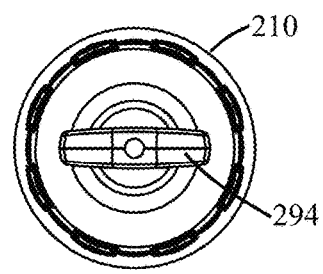
FIG. 8 is a top view of the applicator of FIG. 5.
Figure 9:
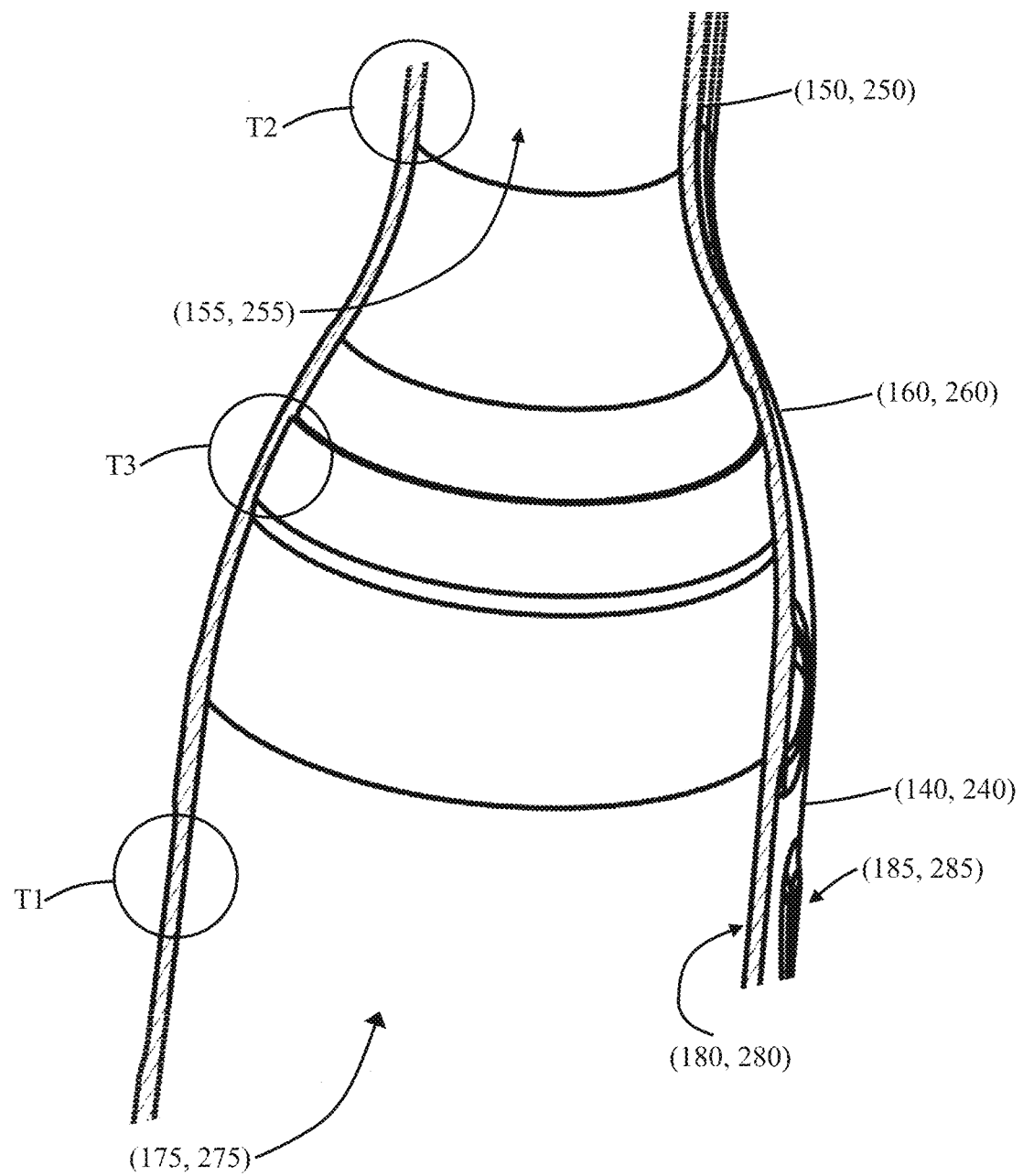
FIG. 9 is a partial cross-sectional view of an applicator according to example embodiments of the present disclosure.
Figure 10:
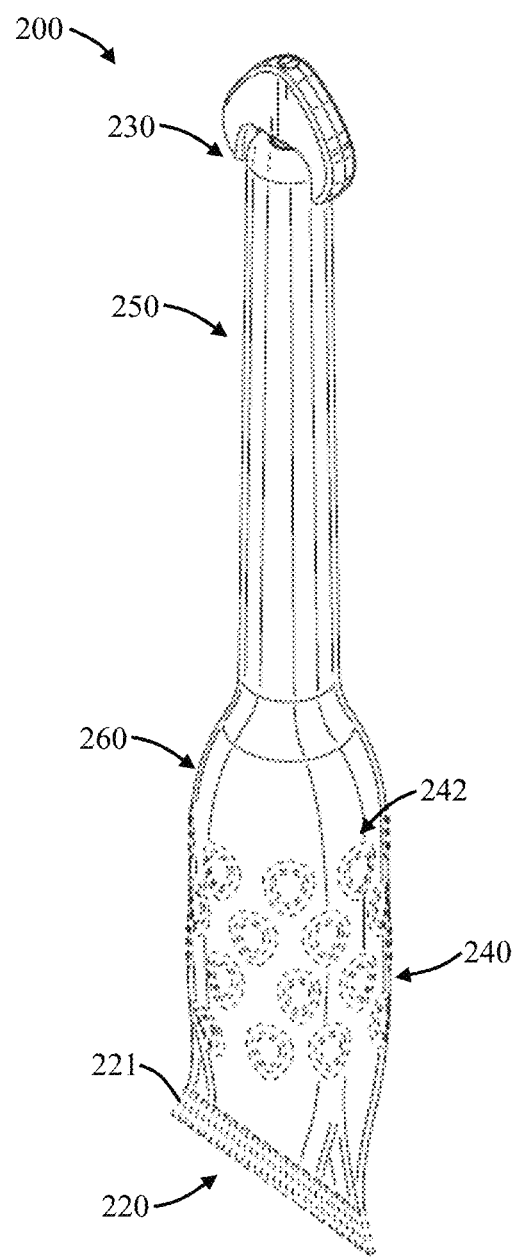
FIG. 10 is a perspective view of an applicator according to an example embodiment of the present disclosure, the applicator including a sealed base end.

The present disclosure relates to applicators adapted to or configured to deliver a product therefrom. The applicators can be particularly designed for delivery to certain body parts of the human body, such as to the vaginal area. Beneficially, the presently disclosed applicators include a number of features that can provide for improved ease of delivery of products, particularly liquid products, with improved comfort to the consumer. Such features are evident in the following discussion provided with reference to FIGS. 1-10. More particularly, FIGS. 1-4 illustrate an embodiment of the presently disclosed applicator 100 with a combination of features, and FIGS. 5-8 illustrate an embodiment of the presently disclosed applicator 200 with a further combination of features. It is understood, however, that one or more features of the embodiment of the applicator 100 illustrated in FIGS. 1-4 may be replaced with one or more features of the embodiment of the applicator 200 illustrated in FIGS. 5-8. Likewise, one or more features of the embodiment of the applicator 200 illustrated in FIGS. 5-8 may be replaced with one or more features of the embodiment of the applicator 100 illustrated in FIGS. 1-4. Further, the features illustrated in FIG. 9 may be included in any embodiments of the applicators (100, 200) that may be envisioned from the elements illustrated in FIGS. 1-8, and any combination thereof. FIG. 10 shows the applicator 200 in a further processed form with a crimped end, and it is understood that any of the embodiments arising from the features illustrated in FIGS. 1-9, or any combination(s) thereof, may likewise be in the further processed form to thus include a crimped end. The ability to arrive at specific embodiments of the invention through mixing of features illustrated in FIGS. 1-10 will be immediately evident to the reader in light of the further disclosure provided below.

In one or more embodiments, an applicator (100, 200) according to the present disclosure can comprising a housing (110, 210) formed of a wall (115, 215). The wall (115, 215) may define the outer boundary of the applicator housing (110, 210) and may further define an interior space (175, 275) (see FIG. 9) within the applicator where a product for delivery may be stored. Such interior space (175, 275) may be referred to as a hollow interior or hollow interior space. The wall (115, 215) may be substantially continuous in nature meaning that the wall may define a housing (110, 210) wherein individual segments thereof are not separable from one another. For example, the housing (110, 210) may be an injection molded part or thermoformed part that is formed as a single piece. Alternatively, one or more segments of the housing (110, 210) may be separably formed and then combined (e.g., via welding, gluing, or the like) such that the one or more segments of the housing are substantially inseparable from one another.

The applicator housing (110, 210), in particular the wall (115, 215), may be formed from any suitable material for providing structural aspects otherwise described herein, including compatibility with the liquid to be stored therein and dispensed therefrom and/or flexibility and compressibility as described herein. For example, the housing, including all or part of the wall, may be formed from a polymeric material, such as a thermoplastic polymer. For example, polyethylene terephthalate (PET), polypropylene (PP), high density polyethylene (HDPE), ultra-high density polyethylene (UHDPE), low density polyethylene (LDPE), polyvinyl chloride (PVC), and similar materials may be utilized.

The housing (110, 210) can be provided with a variety of shapes. In one or more embodiments, the housing (110, 210) can have a substantially round cross-section. More particularly, the substantially round cross-section can be present along substantially an entirety of a length of the housing between the base end (120, 220) and the application end (130, 230). Other cross-sectional shapes may be utilized (e.g., oval, diamond, parallelogram, other non-round shape, etc.), and it is understood that the cross-sectional shape may change from segment to segment. For example, one segment may have a substantially round cross-section while or more of the remaining segments may have a substantially non-round cross-section. For example, the delivery segment (150, 250) may have a substantially round cross-section while one or both of the base segment (140, 240) and the compression segment (160, 260) may have a substantially non-round cross-section.

The wall (115, 215) of the housing (110, 210) may extend along a longitudinal housing axis L between a base end (120, 220) and an application end (130, 230). The housing (110, 210) may be adapted to or configured to have substantially non-uniform dimensions along the length of the housing defined by the longitudinal housing axis L. The non-uniformity may be particularly seen in relation to dimensional differences between the base end (120, 220) and the application end (130, 230). For example, the base end (120, 220) may have a cross-wise dimension, which may be defined as a diameter, a width, or a like dimension, that may be measured substantially perpendicularly to the longitudinal housing axis L. Such dimension may be characterized as a first cross-wise dimension of the housing (110, 210). With reference to FIG. 10, the first cross-wise dimension specifically can be a side-to-side dimension from one end of the substantially linear seal 221 to an opposing end of the substantially linear seal. In other embodiment, however, the first cross-wise dimension may be a diameter or the like at the base end of the applicator prior to sealing thereof. The application end (130, 230) likewise may have a cross-wise dimension, which may be defined as a diameter, a width, or a like dimension, that may be measured substantially perpendicularly to the longitudinal housing axis L. Such dimension may be characterized as a second cross-wise dimension of the housing (110, 210). In some embodiments, the first cross-wise dimension may be greater than the second cross-wise dimension and, likewise, the second cross-wise dimension may be less than the first cross-wise dimension. For example, a ratio of the first cross-wise dimension to the second cross-wise dimension may be about 1.0 to about 10.0, about 1.25 to about 8.0, about 1.5 to about 7.0, about 1.75 to about 6.0, or about 2.0 to about 5.0. In some embodiments, the base end (120, 220) may have a maximum cross-wise dimension of about 1.0 cm to about 5.0 cm, about 1.5 cm to about 4.8 cm, about 2.0 cm to about 4.5 cm, or about 2.25 cm to about 4.25 cm. In further embodiments, the application end (130, 230) may have a maximum cross-wise dimension of about 0.5 cm to about 2.0 cm, about 0.6 cm to about 1.5 cm, or about 0.7 cm to about 1.25 cm.

The substantially continuous wall (115, 215) may define a plurality of individual segments of the housing (110, 210). The individual segments may vary in relation to the function and/or shape and/or dimensions and/or features of the segments even though the overall wall (115, 215) may be continuous. In particular, the substantially continuous wall (115, 215) may define at least a base segment (140, 240), a delivery segment (150, 250), and a compression segment (160, 260).

The base segment (140, 240) can extend from the base end (120, 220) of the housing (110, 210) toward the applicator end (130, 230) and may have a length, for example, of about 1.5 cm to about 8.0 cm, about 1.75 cm to about 7.5 cm, or about 2.0 cm to about 7.0 cm. The dimensions of the base segment (140, 240) may be substantially continuous along the length thereof or may vary along the length thereof. For example, as seen in the figures, the base segment (140, 240) may have a cross-wise dimension that decreases substantially continuously from the base end (120, 220) toward the applicator end (130, 230) of the housing (110, 210). As such, in some embodiments, the base segment (140, 240) may have a substantially frusto-conical shape wherein a lower portion of the base segment (e.g., proximate the base end) has a greater cross-wise dimension that an upper portion of the base segment (e.g., distal from the base end). The base segment (140, 240) preferably can be sized to contain a desired amount of the product to be stored therein. For example, in some embodiments, base segment (140, 240) and delivery segment (150, 250) can be configured to have an internal volume of about 5 $cm^3$ to about 100 $cm^3$, about 10 $cm^3$ to about 70 $cm^3$, or about 15 $cm^3$ to about 50 $cm^3$.

The substantially continuous wall (115, 215) can comprise an interior surface (180, 280) and an exterior surface (185, 285). In some embodiments, at least a portion of the exterior surface (185, 285) may include raised texturing thereon. Although such texturing may be present on any part of the exterior surface (185, 285) of the substantially continuous wall (115, 215), it can be preferred for the raised texturing to be present on at least a portion of the base segment (140, 240) thereof. In some embodiments, such texturing may be expressly absent from one or both of the delivery segment (150, 250) and the compression segment (160, 260). The raised texturing may be expressly distinguishable from an engraved texturing where portions of the wall surface are removed. The raised texturing thus extends outward from the exterior surface (185, 285) of the substantially continuous wall (115, 215). The raised texturing can be adapted to or configured to improve the ability of a consumer to grasp or hold the applicator (100, 200) during use thereof. As seen in the figures, raised texturing (142, 242) can preferably be adapted to or configured to be aligned substantially orthogonally to the longitudinal housing axis L. More particularly, the raised texturing (142, 242) can comprise lining that is oriented in directions other than parallel to the longitudinal housing axis L. Such non-parallel orientation relative to the longitudinal housing axis L can be beneficial to improve the ability of a consumer to grasp the applicator (100, 200) during use. In the examples seen in FIG. 1 through FIG. 3, the raised texturing 142 can be curvilinear so as to define a substantially wavy pattern around at least a portion of the base segment (140, 240). In the examples seen in FIG. 5 through FIG. 7, the raised texturing 242 can define a geometric pattern around at least a portion of the base segment (140, 240) wherein a majority of the lines forming the geometric pattern are oriented substantially orthogonally to the longitudinal housing axis L. The illustrated raised texturing (142, 242) is exemplary, and it is understood that other shapes and/or patterns may be utilized.

The delivery segment (150, 250) can extend from the applicator end (130, 230) of the housing (110, 210) toward the base end (120, 220) and may have a length, for example, of about 2.0 cm to about 12.0 cm, about 3.0 cm to about 11.0 cm, about 4.0 cm to about 10.0 cm, or about 5.0 cm to about 9.0 cm. The dimensions of the delivery segment (150, 250) may be substantially continuous along the length thereof or may vary along the length thereof. For example, the delivery segment (150, 250) may have a diameter that varies between about 0.2 cm to about 2.5 cm, about 0.3 cm to about 2.0 cm, or about 0.4 cm to about 1.8 cm. Further, the delivery segment (150, 250) may define an inner channel (155, 255) bounded by the interior surface (180, 280) of the substantially continuous wall (115, 215). The inner channel (155, 255) preferably has overall dimensions that provide for ease of passage of the product therethrough that is stored within the applicator (100, 200).

The compression segment (160, 260) may be adapted to or configured to interconnect the base segment (140, 240) and the delivery segment (150, 250). The compression segment (160, 260) otherwise may be characterized as a section of the substantially continuous wall (115, 215) that is present between the base segment (140, 240) and the delivery segment (150, 250). In some embodiments, the compression segment (160, 260) may be specifically formed to provide for ease of compression of the substantially continuous wall (115, 215) relative to the other segments of the substantially continuous wall. For example, in some embodiments, the substantially continuous wall (115, 215) can have a thickness that varies along a length of the longitudinal housing axis L. Preferably, the thickness of the substantially continuous wall (115, 215) can be less in at least a portion of the compression segment (160, 260) than in any part of one or both of the base segment (140, 240), and the delivery segment (150, 250). As seen in FIG. 9, the substantially continuous wall (115, 215) has a first thickness (T1) in the base segment (140, 240), has a second thickness (T2) in the delivery segment (150, 250), and has a third thickness (T3) in the compression segment (160, 260). In the illustrated embodiments, T3 is less than T2 and is less than T1. In some embodiments, T1 and T2 may be different or may be substantially identical; however, it is preferred for T3 to be less than both T1 and T2 for at least a portion of the compression segment (160, 260). A ratio between T3 and T1 and a ratio between T3 and T2 can be, for example, about 0.2 to about 0.9, about 0.3 to about 0.8, or about 0.4 to about 0.7. In some embodiments, the wall thickness in around the area of T1 may be about 0.4 mm to about 0.6 mm or about 0.45 mm to about 0.55 mm, the wall thickness in around the area of T2 may be about 0.5 mm to about 0.8 mm, or about 0.55 mm to about 0.75 mm, and the wall thickness in around the area of T3 may be about 0.25 mm to about 0.45 mm or about 0.3 mm to about 0.42 mm. By having the thickness of the substantially continuous wall (115, 215) in the compression segment (160, 260) be less than the thickness of the substantially continuous wall in other portions of the housing (110, 210), the compressibility of said section may be improved, thus making it easier for a consumer to compress the compression segment with sufficient force to expel the product that is stored within the housing. The compression segment (160, 260) may differ from one or both of the base segment (140, 240) and the delivery segment (150, 250) in relation to the shape of the segment. For example, the substantially continuous wall (115, 215) in the compression segment (160, 260) can be substantially curvilinear along the length of the longitudinal housing axis L. On the other hand, the substantially continuous wall (115, 215) in one or both of the base segment (140, 240) and the delivery segment (150, 250) can be substantially linear along the length of the longitudinal housing axis L.

In one or more embodiments, the various segments of the housing (110, 210) may vary in length. Preferably, the housing (110, 210) can have a total length in the range of about 4 cm to about 20 cm, about 6 cm to about 18 cm, or about 8 cm to about 16 cm. Each of the individual segments of the applicator (100, 200) may be defined in relation to the total length of the applicator. For example, in some embodiments, the delivery segment (150, 250) may form about 50% or greater of the total length of the housing (110, 210), such as in the range of about 50% to about 75%, about 55% to about 70%, or about 55% to about 65% of the total length of the housing. In some embodiments, the base segment (140, 240) can comprise about 40% or less of the total length of the housing (110, 210), such as in the range of about 15% to about 40%, about 20% to about 40%, or about 25% to about 40% of the total length of the housing. In some embodiments, the compression segment can comprise about 5% to about 30%, about 10% to about 30%, or about 15% to about 30% of the total length of the housing (110, 210).

In some embodiments, the applicator of the present disclosure can be adapted to or configured to deliver liquid products having a wide viscosity range. As such, the housing of the applicator may be pre-filled with a liquid product. More particularly, a liquid product suitable for use with the applicator can be a lubricant, such as a vaginal lubricant. Lubricating materials and other liquid products suitable for use with the present applicator may exhibit relatively high viscosities due to the nature of the lubricating materials used to form such products. Whereas known applicators may be limited in relation to the viscosity of a liquid that may be used therewith, the presently disclosed applicator can be effective for relatively easy delivery of liquids with relatively high viscosities without the necessity of undue compressive forces being required. It is understood that high viscosity liquids may be deliverable through application of high compressive forces; however, many consumers may be unable to apply the necessarily high compressive forces required to expel a high viscosity liquid, especially when the applicator is positioned for delivery to a somewhat difficult to reach part of the body. Because of the overall structure of the presently disclosed application, particularly the structure of the compression segment, the present applicator can be adapted to or configured to deliver a liquid product having a viscosity across a substantially large range while only requiring a limited amount of compressive force. For example, in some embodiments, the presently disclosed applicator can be adapted to or configured to deliver a liquid product having a viscosity of about 100 cP to about 300,000 cP, about 1,000 cP to about 250,000 cP, about 1,500 cP to about 225,000 cP, or about 2,500 cP to about 200,000 cP without requiring excessive forces to be applied by the consumer.

The applicator (100, 200) can be configured so that the base end 220 can have a variety of shapes and structures. In some embodiments, the base end 220 may be substantially so as to define a bottom surface. In order to minimize materials needed for forming a single applicator, however, the base end 220 may be crimped and sealed. In this manner, the applicator 200 may be easily filled with liquid product by inverting the applicator so that the applicator is substantially in an upside down orientation and delivering the desired volume of liquid into the applicator. Pressure may then be applied in the area of the base end 220 from opposing sides in a direction that is substantially transverse to the longitudinal axis of the applicator so that the base end is pressed together to form a substantially linear seal 221 at the base end, as shown in FIG. 10. Sealing can be carried out by any suitable method, including gluing, welding, and/or heat sealing. In particular, since the applicator 200 may be formed of a polymeric material, sealing may be achieved by crimping the wall of the applicator at the base end under heating to form a crimped seal 221. In FIG. 10, the substantially linear seal 221 extends side-to-side so that the base end 220 is substantially flat, and the base segment 240 of the applicator 200 angles outwardly from the substantially linear seal to define a rounded shape. As such, the sealed applicator can be defined so that the base segment 240 has a width (side-to-side) that is greater than a thickness thereof. Further, the processing of the applicator by starting with a structure having a substantially round cross-section as the base end 220 and compressing to form the substantially linear seal 221 can cause the applicator to have a substantially flared shape (side-to-side) in the base segment 240 when viewing from the front or rear of the applicator. The substantially linear seal 221 can have a height that is about 1% to about 10%, about 1.5% to about 8%, or about 2% to about 6% of the total height or length of the applicator 200. The raised texturing 242 is illustrated in broken lines in FIG. 10 as illustrating that such texturing can take on any desired shape as otherwise discussed herein. Similarly, the substantially linear seal 221 is illustrated in broken lines indicating that such seal can have a variety of textures, such as being substantially flat, being ribbed, exhibiting knurling, or having any other texturing that may be purposely added or that may arise from the sealing process. When utilizing a sealing technique as noted above where the base end is compressed and sealed, the structure of the applicator as seen FIGS. 1-8 can be characterized as being a blank, and the structure of the applicator as seen in FIG. 10 can be characterized as being a finished and filled product. An applicator blank thus may have a substantially open base end, and a finished and filled applicator can have a base end with a substantially linear seal 221.

In addition to the foregoing, the presently disclosed applicator (100, 200) can further comprise a closure (190, 290) positioned at the application end (130, 230) of the housing (110, 210). The closure (190, 290) can be removable through any desired means. Preferably, the closure (190, 290) can be integrally formed with the substantially continuous wall (115, 215) so as to be separable therefrom, such as being in the form of a snap-off or twist-off cap or tab. This may be achieved through the presence of a weakened portion of the substantially continuous wall (115, 215) between the delivery segment (150, 250) and the closure (190, 290) that gives way when the closure is bent or twisted relative to the remainder of the housing (110, 210). In other embodiments, however, other closures may be utilized, including closures that are separately formed, such as a threaded cap, or the like.

The closure (190, 290) can be adapted to or configured to include a substantially central post (192, 292) extending from the application end (130, 230) of the housing (110, 210) and one or more gripping walls (194, 294) extending from the substantially central post. In some embodiments, the one or more gripping walls (194, 294) may extend upward and/or outward from the substantially central post (192, 292) and may be integrally formed therewith. Gripping and twisting, bending, or the like of the gripping walls (194, 294) can be effective to disengage the closure (190, 290) from the application end (130, 230) of the housing (110, 210).

The closure (190, 290) may have dimensions that can improve the ease of opening of the applicator (100, 200). In some embodiments, this may relate to the absolute dimensions of the closure (190, 290). For example, the closure (190, 290) can be characterized has having a height that is substantially parallel to the longitudinal housing axis L and a width that is substantially transverse to the longitudinal housing axis. Further, the closure (190, 290) can be adapted to or configured to have a width that is greater than the second cross-wise dimension of the housing at the application end (130, 230) of the housing (110, 210). Such width also can be defined relative to the base end (120, 220) of the housing (110, 210). For example, the width of the closure (190, 290), and more particularly the width of the gripping wall(s) (194, 294), can be about 5% to about 100% of the first cross-wise dimension of the housing (110, 210) at the base end (120, 220) of the housing.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. An applicator for delivery of a product therefrom, the applicator comprising:
　a housing formed of a substantially continuous wall extending along a longitudinal housing axis between a base end having a first cross-wise dimension and an application end having a second cross-wise dimension that is less than the first cross-wise dimension, the substantially continuous wall defining:
　a base segment extending from the base end toward the applicator end;
　a delivery segment extending from the applicator end toward the base end; and
　a compression segment interconnecting the base segment and the delivery segment;
　wherein the housing defines a substantially hollow interior configured for retaining a product for delivery through the delivery segment,
　wherein the substantially continuous wall has a thickness in the compression segment that is less than a thickness of the substantially continuous wall in at least the base segment.

2. The applicator of claim 1, wherein the substantially continuous wall comprises an exterior surface, and wherein at least a portion of the exterior surface of the base segment includes raised texturing thereon.

3. The applicator of claim 2, wherein the raised texturing is aligned substantially orthogonally to the longitudinal housing axis.

4. The applicator of claim 1, wherein the substantially continuous wall has a thickness that varies along a length of the longitudinal housing axis.

5. The applicator of claim 4, wherein the substantially continuous wall has the thickness in the compression segment that is less than the thickness of the substantially continuous wall in both of the base segment and the delivery segment.

6. The applicator of claim 1, wherein the substantially continuous wall in the compression segment is substantially curvilinear along the longitudinal housing axis.

7. The applicator of claim 1, wherein the substantially continuous wall in one or both of the base segment and the delivery segment is substantially linear along the longitudinal housing axis.

8. The applicator of claim 1, wherein the housing has a total length, and wherein the delivery segment forms about 50% or greater of the total length of the housing.

9. The applicator of claim 8, wherein the base segment comprises about 40% or less of the total length of the housing.

10. The applicator of claim 8, wherein the compression segment comprises about 5% to about 30% of the total length of the housing.

11. The applicator of claim 1, wherein the base segment is configured to have an internal volume of about 5 cm$^3$ to about 100 cm$^3$.

12. The applicator of claim 1, wherein the applicator is configured for delivery of a liquid product having a viscosity of about 100 cP to about 300,000 cP.

13. The applicator of claim 1, wherein the applicator further comprises a removable closure positioned at the application end of the housing.

14. The applicator of claim 13, wherein the removable closure is configured as a twist-off tab.

15. The applicator of claim 14, wherein the twist-off tab has a height that is substantially parallel to the longitudinal housing axis and a width that is substantially transverse to the longitudinal housing axis.

16. The applicator of claim 15, wherein the width of the twist-off tab is greater than the second cross-wise dimension of the housing at the application end of the housing.

17. The applicator of claim 15, wherein the width of the twist-off tab is about 5% to about 100% of the first cross-wise dimension of the housing at the base end of the housing.

18. The applicator of claim 1, wherein the housing has a substantially round cross-section along at least a portion thereof.

19. The applicator of claim 1, wherein the base end comprises a substantially linear seal.

20. The applicator of claim 1, wherein the housing is pre-filled with a liquid product.

21. The applicator of claim 1, wherein the liquid product is a vaginal lubricant.

* * * * *